United States Patent [19]
Sakamoto et al.

[11] Patent Number: 6,142,945
[45] Date of Patent: Nov. 7, 2000

[54] BALLOON ANCHOR FOR ENDOSCOPICALLY INSERTING ULTRASOUND PROBE

[75] Inventors: Toshio Sakamoto; Toshizumi Tanaka; Hiromu Itoi, all of Omiya, Japan

[73] Assignee: Fuji Photo Optical Co., Ltd., Omiya, Japan

[21] Appl. No.: 09/196,126

[22] Filed: Nov. 20, 1998

[30] Foreign Application Priority Data

Nov. 26, 1997 [JP] Japan ..................................... 9-339505
Dec. 2, 1997 [JP] Japan ..................................... 9-345759
Mar. 27, 1998 [JP] Japan ................................... 10-098135
Mar. 31, 1998 [JP] Japan ................................... 10-101843

[51] Int. Cl.[7] ........................................................ A61B 8/00
[52] U.S. Cl. ............................................................. 600/459
[58] Field of Search ..................................... 600/454, 462, 600/463, 465, 467, 466, 470

[56] References Cited

U.S. PATENT DOCUMENTS 5,178,150  1/1993  Silverstein et al. ..................... 600/462
5,331,947  7/1994  Shturman .................................. 600/466
5,474,071  12/1995  Chapelon et al. ....................... 600/467

*Primary Examiner*—Marvin M. Lateef
*Assistant Examiner*—Maulin Patel
*Attorney, Agent, or Firm*—Oblon, Spivak, McClelland, Maier & Neustadt, P.C.

[57] ABSTRACT

A balloon anchor for use with an endoscopically inserting ultrasound probe having an ultrasound transducer element accommodated in an ultrasound scanner head at the fore distal end of a flexible cord to be placed in an endoscopic biopsy channel. The balloon anchor includes an anchor tube which is adapted to be fitted in the endoscopic biopsy channel in such a way that it is partly projected from fore distal end of the endoscopic biopsy channel. Connected to the projected fore end of the anchor tube is a balloon support member of a larger diameter as compared with the endoscopic biopsy channel. A passage of a large diameter is formed axially through the anchor tube and through the balloon support member. A balloon stopper portion is provided on the outer periphery of the balloon support member to anchor a resilient ring of a balloon therein.

17 Claims, 15 Drawing Sheets

BALLOON ANCHOR FOR ENDOSCOPICALLY INSERTING ULTRASOUND PROBE

BACKGROUND OF THE INVENTION

1. Field of the Art

This invention relates to a balloon anchor for an endoscopically inserting ultrasound probe of an ultrasound examination system, more particularly, to a balloon anchor for stopping a balloon fixedly and hermetically on and around an ultrasound scanning head which is designed to be introduced into a body cavity through a biopsy or instrument channel usually provided on an endoscope for insertion of forceps or other surgical or biopsy instruments.

2. Prior Art

Ultrasound examination systems are largely constituted by an ultrasound probe with an ultrasound transducer element and an ultrasound image observation terminal. Through the ultrasound transducer element of the probe which is positioned face to face with a body portion of interest, ultrasound pulses are transmitted into the body portion under examination, and at the same time return echoes are converted into electrical signals by the transducer element. The return echo signals from the ultrasound transducer element are transferred to the ultrasound image observation terminal and processed into video signals by predetermined signal processing operations well known in the art to display ultrasound images on a monitor screen.

In addition to external or percutaneous scan type ultrasound probes, there have been in use internal or intracavitary scan type ultrasound probes which are designed to be inserted into a body cavity and to transmit and receive ultrasound signals through an intracavitary wall. In the case of the internal or intracavitary scan type, the ultrasound probe has an ultrasound transducer element mounted on an ultrasound scanning head at the distal end of a narrow flexible cord. The flexible cord is disconnectibly connectible to an ultrasound image observation terminal through a connector means which is provided at its base or tail end.

The internal scan type ultrasound probes which are designed for direct ultrasound transmission and reception through an intracavitary wall have an advantage that an intracavitary portion under examination can be scanned from a very close position. For insertion into a body cavity, some ultrasound probes are designed to be inserted directly into a canal or duct leading to a body cavity of interest, while some other ultrasound probes are designed to be introduced into a body cavity by way of a guide means which has been inserted into the body cavity of interest beforehand. In case an endoscope is used as a guide means for an ultrasound probe, it becomes possible to carry out an overall examination or diagnosis on an intracavitary portion of interest, firstly examining the intracavitary portion through the endoscope and, if a diseased or suspicious portion is spotted by the use of the endoscope, making an ultrasound scan while monitoring the ultrasound probe through the endoscopic observation system. A biopsy or instrument channel which is usually provided on an endoscope is used as a guide means for introducing an ultrasound probe into a body cavity.

For placement in an endoscopic biopsy channel, the flexible cord of an ultrasound probe of this sort has to be thinner than the inside diameter of the endoscopic biopsy channel. Nevertheless, either the ultrasound scanning head or the connector which is attached to the head or tail end of the flexible cord may have a diameter larger than the endoscopic biopsy channel. In case the ultrasound scanning head is larger than the endoscopic biopsy channel in diameter, the ultrasound probe is placed in the endoscopic biopsy channel from its tail end before inserting the endoscope into a body cavity. On the other hand, in case the ultrasound scanning head of the probe is smaller in diameter than the endoscopic biopsy channel, the ultrasound probe can be placed in the endoscopic biopsy channel after inserting the endoscope into a body cavity to be examined.

At the time of an ultrasound scanning operation, an air gap in a path of ultrasound signals between an ultrasound transducer element and an intracavitary wall under examination could attenuate the signals to a considerable degree. In order to avoid this problem, it has been the general practice to fit on and around an ultrasound scanning head of a probe a balloon which is filled with an ultrasound transmitting medium. A balloon of this sort is composed of a flexible membrane of elastic material such as latex or the like, and a resilient stopper ring which stops the balloon on an ultrasound scanning head of a probe in a sealed state. The flexible membrane is in some cases in the shape of a bag which is closed at its fore end and open at its base end to be fitted and anchored on an ultrasound scanning head of a probe by a resilient ring. The flexible membrane of the balloon may be of a cylindrical shape which is open at its opposite ends and designed to be anchored on an ultrasound scanning head of a probe by means of a couple of resilient stopper rings.

Provided on the circumferential surface of an ultrasound scanning head of a probe is one or two annular grooves for anchoring the above-mentioned resilient stopper ring or rings. The flexible membrane of a balloon which is fitted on an ultrasound scanning head of a probe is hermetically sealed at its open end or ends as the resilient stopper ring or rings are engaged with the annular groove or grooves on the side of the ultrasound scanning head. After putting on a balloon, the ultrasound probe is inserted into a biopsy channel of an endoscope and protruded into a body cavity through an opening at the fore end of the endoscopic biopsy channel. Thereafter, an ultrasound transmitting medium is fed to the balloon on the ultrasound scanning head, filling and inflating the balloon with the ultrasound transmitting medium to a certain degree. As an ultrasound transmitting medium, for example, deaerated water or the like can be suitably used for this purpose.

During transmission and reception of ultrasound signals, the balloon which is filled and inflated with an ultrasound transmitting medium is held in intimate contact with an intracavitary wall. For instance, the sites of internal ultrasound examination by a probe usually include a narrow duct like the esophagus as well as the stomach and other internal organs. In case of an ultrasound examination within a narrow duct, the balloon can be brought into intimate contact with an intracavitary wall without sending a large quantity of ultrasound transmitting medium into the balloon. However, for bringing the balloon into intimate contact with an intracavitary wall within a body cavity which has a broad space like the stomach, it becomes necessary to inflate it to a greater degree by sending thereinto a larger amount of ultrasound transmitting medium.

The ultrasound scanning head of the probe, which is to be fitted with a balloon, normally has a rigid structure for accommodation of an ultrasound transducer element. For insertion into an endoscopic biopsy channel, the ultrasound probe is arranged to have a very small diameter even at the ultrasound scanning head, and to have a minimum necessary length in the axial direction. Accordingly, the flexible membrane and resilient stopper ring or rings of a balloon to be fitted on the ultrasound scanning head of a probe are also restricted in dimensions. Besides, since an ultrasound transducer element is accommodated in the ultrasound scanning head, the depth and width of the annular grooves which are provided on the scanning head for anchoring the resilient stopper rings are subject to similar dimensional restrictions. As a consequence, in some cases a limitation is put on the amount of ultrasound transmitting medium to be supplied to the balloon, making it difficult to hold the balloon in intimate contact with an intracavitary wall under observation over a broad area. In addition to limitation of a feasible ultrasound scanning range, due to insufficient anchoring strength of a resilient stopper ring, there has been a problem of dislocation of the resilient stopper ring out of the annular groove on the ultrasound scanner head under the weight of the supplied ultrasound transmitting medium. These problems occur more conspicuous especially in case of an endoscopically inserting type ultrasound probe which requires a balloon with flexible membrane and resilient ring of smaller sizes for passage through a biopsy channel of an endoscope.

SUMMARY OF THE INVENTION

With the foregoing situations in view, it is an object of the present invention to provide a balloon anchor device which is capable of holding a balloon securely and hermetically with an increased force on and around an ultrasound scanning head of a thin endoscopically inserting ultrasound probe which is designed to be introduced into a body cavity through a biopsy or instrument channel of an endoscope or the like, permitting to inflate the balloon in a greater degree by introduction thereinto of a larger amount of ultrasound transmitting medium whenever necessary.

It is another object of the present invention to provide a balloon anchor of the sort as mentioned above, which permits to put a balloon of a large capacity on an ultrasound scanning head of a probe in a facilitated manner and which can anchor the balloon stably in position on the ultrasound scanning head.

It is still another object of the present invention to provide a balloon anchor of the sort as mentioned above, which can securely prevent air from sneaking into a balloon fitted on an ultrasound scanning head of a probe.

In accordance with the present invention with the objectives as stated above, there is provided a balloon anchor for use with an endoscopically inserting ultrasound probe for stopping a balloon fixedly and hermetically on and around an ultrasound scanner head of the probe which is placed in a biopsy channel of an insertion instrument of an endoscope at the time of an ultrasound scan within a body cavity. The balloon anchor according to the invention basically comprises: an anchor tube member adapted to receive the flexible cord of the ultrasound probe therein and to be placed in the endoscopic biopsy channel along with the flexible cord, the anchor tube member having a fore end portion projected through an opening at distal fore end of the endoscopic biopsy channel; a balloon support member connected to the projected fore end of the anchor tube member and having a cylindrical body of a diameter larger than the endoscopic biopsy channel; a fluid passage formed around the flexible cord in the anchor tube member and axially through the balloon support member; and a balloon stopper portion provided on outer periphery of the balloon support member to stop therein a resilient ring of the balloon.

Preferably, the balloon support member is provided with one or a plural number of radial communication ports which are each in communication with the axial passage and opened on the outer periphery of the balloon support member at a position forward of an annular stopper groove of the balloon stopper portion. More preferably, the axial passage of the balloon support member is diverged toward its fore end in a tapered fashion, and the radial communication ports are opened in the diverged fore end portion of the axial passage to ensure efficient flow of ultrasound transmitting medium into a balloon.

In one preferred form of the invention, the anchor tube is constituted by a flexible tube which is passed coextensively through an endoscopic biopsy channel and has a liquid feed section connected to its proximal end portion which is led out of the endoscopic biopsy channel. Alternatively, the anchor tube may be arranged to be fitted into an endoscopic biopsy channel over a predetermined length from a fore distal end of the biopsy channel.

Further, preferably an air escape mechanism is provided either on the balloon support member or on an end cap of the ultrasound scanner head of the probe for expelling air out of a balloon anchored in position on and around the ultrasound scanner head.

The above and other objects, features and advantages of the present invention will become apparent from the following particular description based on preferred embodiments shown in the accompanying drawings. However, it is to be understood that the present invention is not restricted to specific forms shown in the drawings, which are adopted for illustrative purposes only.

DESCRIPTION OF PREFERRED EMBODIMENTS

Figure 1:
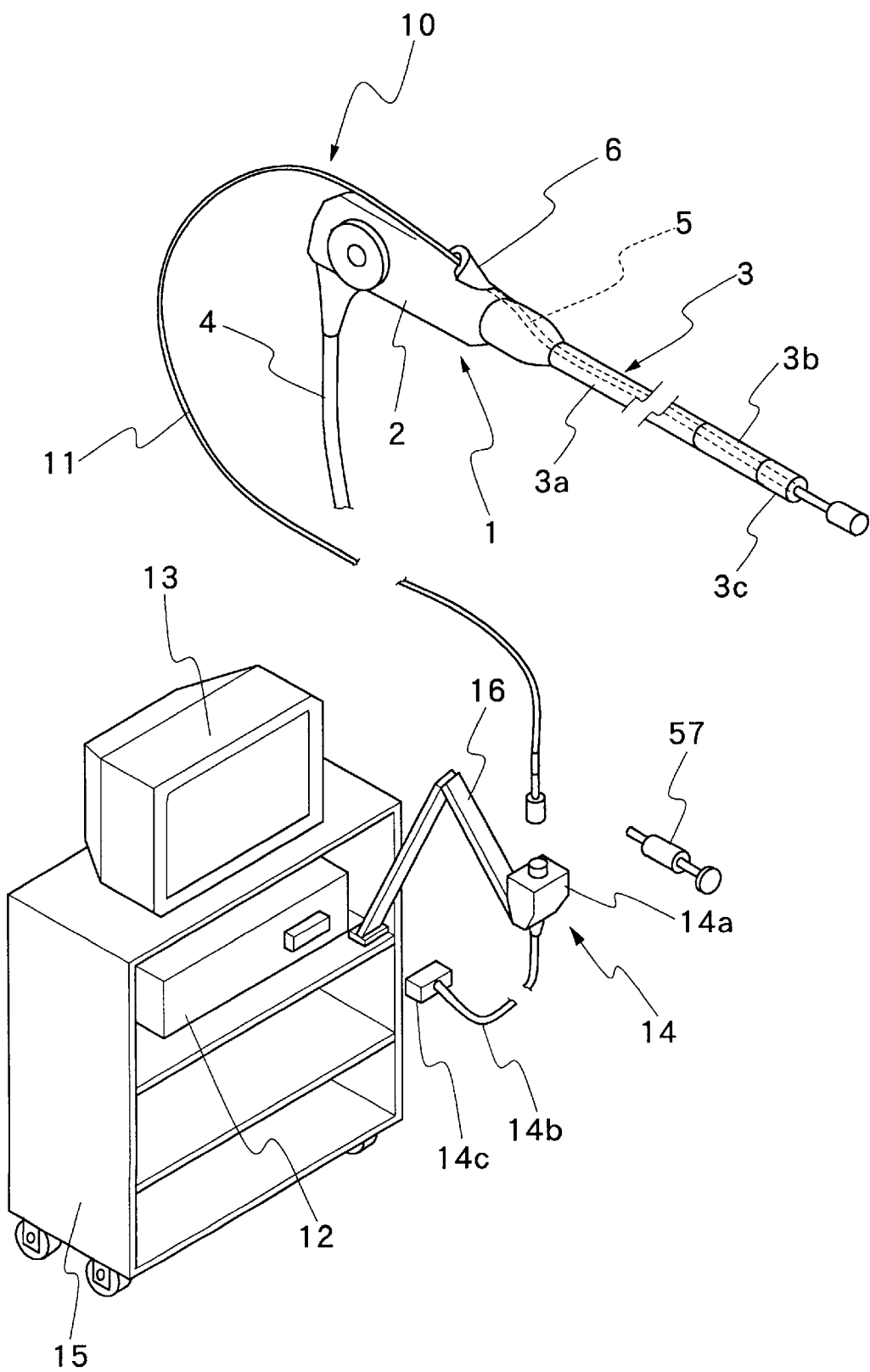
FIG. 1 is a schematic outer view of an ultrasound examination system having an ultrasound probe placed in a biopsy channel of an endoscope.

Hereafter, the present invention is described more particularly by way of its preferred embodiments shown in the drawings. Referring first to FIG. 1, there is shown the general layout of an ultrasound examination system along with an endoscope which serves as a guide in introducing an ultrasound probe into a body cavity. In that figure, the endoscope and the ultrasound examination system are indicated at 1 and 10, respectively.

The endoscope 1 is largely constituted by a manipulating head grip 2 to be gripped by an operator, an insertion instrument 3 to be inserted into a body cavity, and an universal cable which is disconnectibly connected to a light source. The insertion instrument 3 includes a flexible rod section 3a, which occupies a major part of the entire length of the insertion instrument 3 and extends forward from a proximal end which is connected to the manipulating head grip 2, and a angle section 3b and a rigid tip end section 3c which are successively connected to the fore end of the flexible rod section 3a. The universal cable 4 is disconnectibly connected to a light source (or to a light source and a signal processor in the case of an electronic endoscope), and has at least a light guide passed therethrough to transmit illumination light from the light source to the rigid tip end section 3c. Provided on the fore end face (or on a lateral side of a fore end portion) of the rigid tip end section 3c are endoscopic observation means including an illumination light emitting portion and an image pickup portion although these portions are omitted in the drawings for the sake of simplicity of illustration. Besides, a fore end of a biopsy channel 5, which is provided internally of the endoscopic insertion instrument 3 for insertion of forceps or other surgical or bioptic instruments, is opened in the fore end face of the rigid tip end section 3c. The biopsy channel 5 is extended from the distal end of the insertion instrument 3 up to the manipulating head grip 2 of the endoscope, and connected with an instrument entrance housing 2 which is provided on the manipulating head grip 2 for an instrument to be inserted into the biopsy channel 5.

The ultrasound examination system 10 is largely constituted by an ultrasound probe 11, and an ultrasound image observation terminal with a processor for producing ultrasound images on the basis of received return echoes and a monitor screen for displaying produced ultrasound images. The ultrasound probe 11 is disconnectibly connected to the ultrasound image observation terminal 12 through a relay means 14. The relay means 14 is constituted by a scanner drive unit 14a, a cable 14b and a connector 14c. The connector 14c is detachably connectibe to the ultrasound image observation terminal 12. The proximal end of the ultrasound probe 11 is disconnectibly connected to the scanner drive unit 14a which houses within its casing a radial scan drive motor along with an encoder. The scanner drive unit 14a is supported on an arm 16 which is pivotally supported on a monitor rack 15 of the ultrasound image observation terminal 12. The arm 16 can be turned to an arbitrary direction by an operator.

Figure 2:
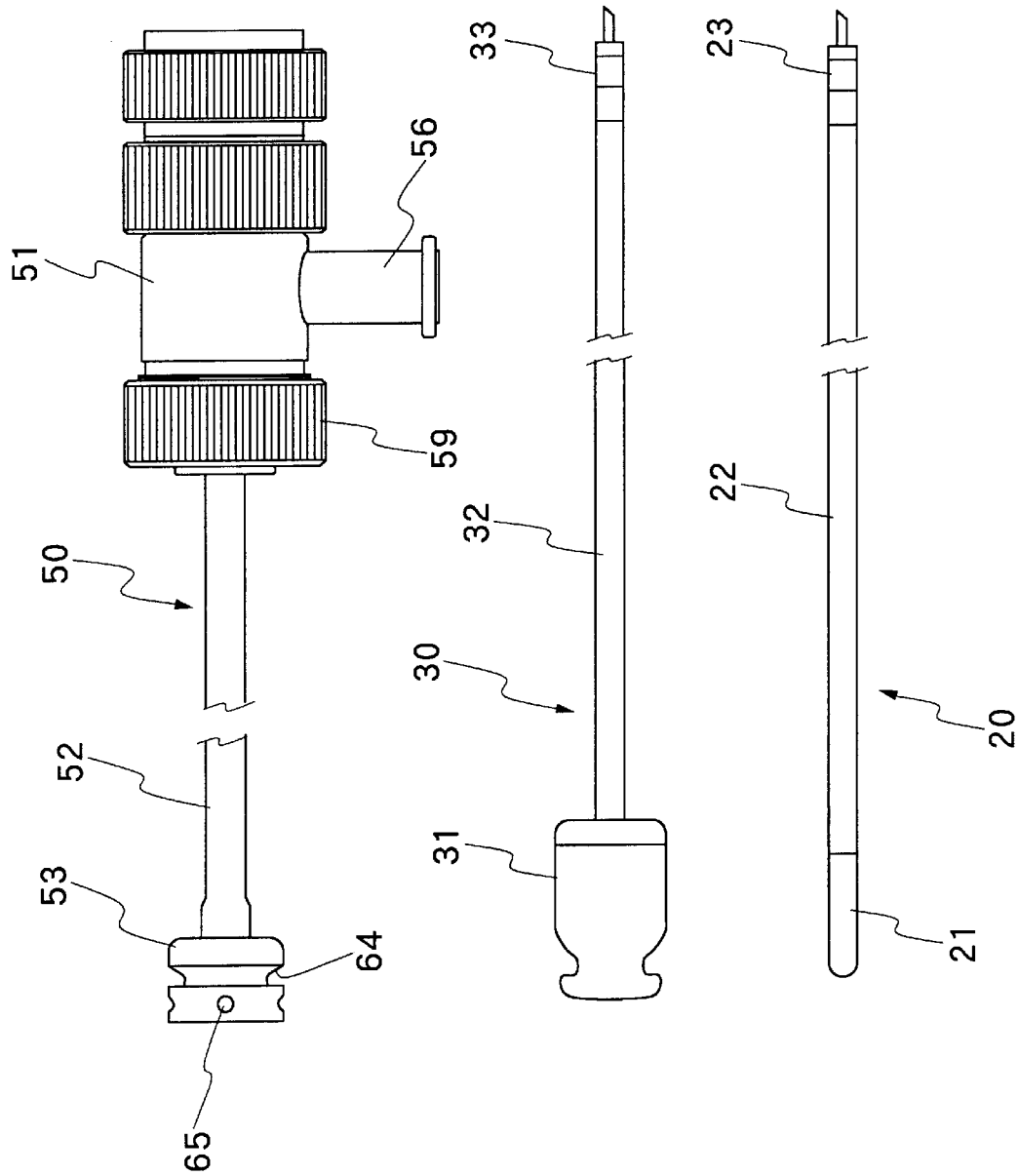
FIG. 2 is a plan view of a balloon anchor device and ultrasound probes of two different types which can be fitted into the balloon anchor device.

As mentioned hereinbefore, the ultrasound probe 11 is introduced into a body cavity through a biopsy channel of an endoscope. FIG. 2 shows two different types of endoscopically inserting ultrasound probes. The first small-head type ultrasound probe, which is indicated at 20, is provided with a ultrasound scanner head 21, a flexible cord 22 and a tail end connector 23 from its fore distal end to proximal end. In this case, the ultrasound scanner head 21 has the same outside diameter as the flexible cord 22. On the other hand, the second large-head type ultrasound probe, which is indicated at 30 is provided with, from its fore distal end, an ultrasound scanner head 31, a flexible insertion rod 32, and a tail end connector 33. In this case, the ultrasound scanner head 31 has a larger outside diameter than the flexible cord 32.

The flexible cords 22 and 32 of these ultrasound probes 20 and 30 have an outside diameter smaller than the inside diameter of the endoscopic biopsy channel 5. The ultrasound probe 20 has the ultrasound scanner head 21 formed in a smaller diameter than the endoscopic biopsy channel 5, while the ultrasound probe 30 has the tail end connector 33 formed in a smaller diameter than the endoscopic biopsy channel 5. Namely, the tail end connector 23 of the ultrasound probe 20 and the scanner head 31 of the ultrasound probe 30 are not necessarily required to be formed in a smaller diameter than the endoscopic biopsy channel 5. It follows that, for the purpose of improving ultrasound signal transmission and reception characteristics, the diameter of the ultrasound scanner head 31 of the probe 30 can be increased within a range which will not obstruct the insertion of the flexible insert rod 3 of the endoscope 1. In contrast, from the standpoint of strength in use, ultrasound probe 20 may have the tail end connector 23 formed in a larger diameter. However, for the sake of simplicity of explanation, the tail end connectors 23 and 33 of the ultrasound probes 20 and 30 are regarded as being of the same construction in the following description.

Figure 3:
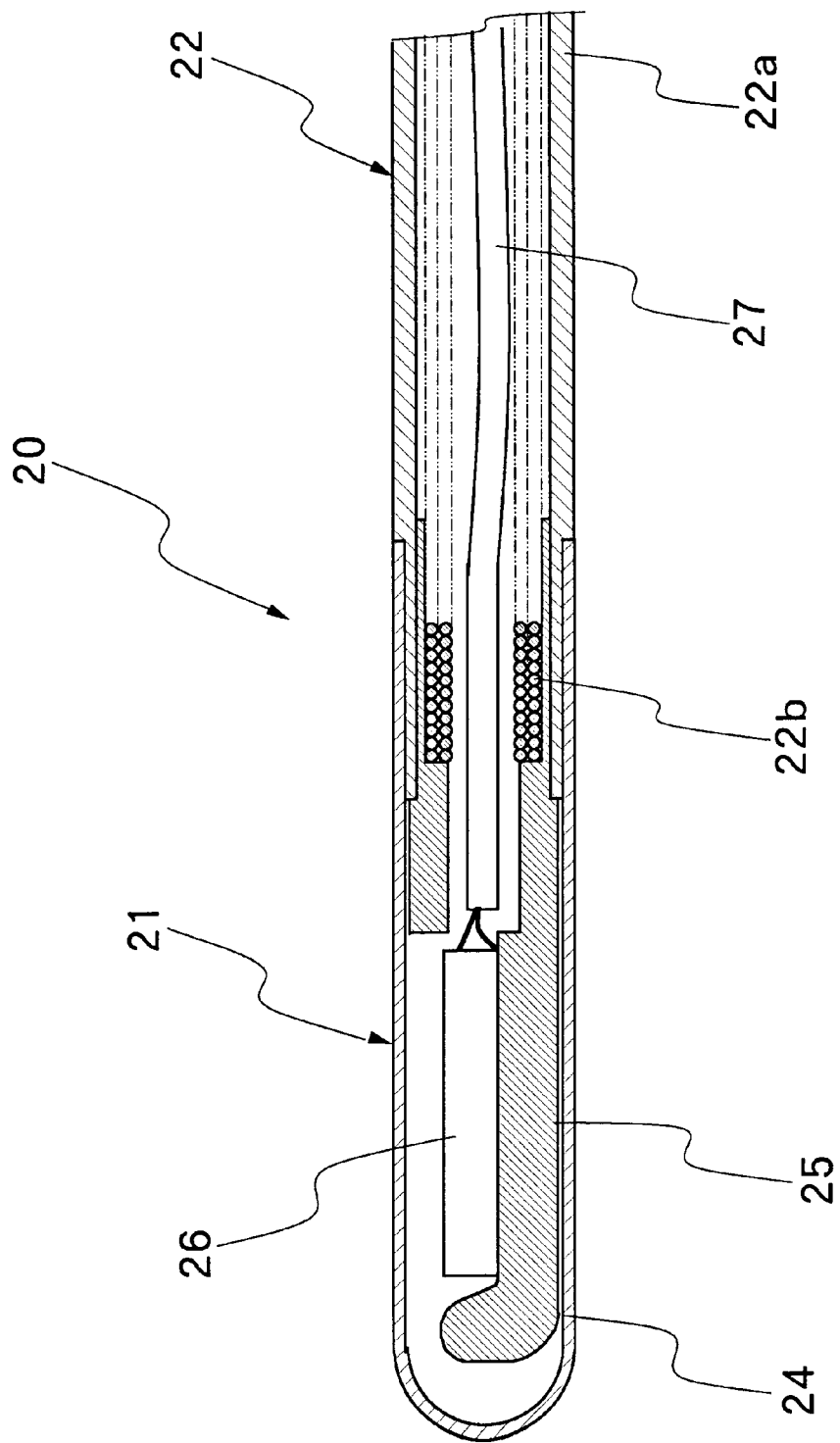
FIG. 3 is a schematic sectional view of a fore end portion of a first type of ultrasound probe.

FIG. 3 shows the construction of the scanner head 21 of the ultrasound probe 20 of the first type. As seen in that figure, the ultrasound scanner head 21 is provided with a thin-walled end cap 24 which is formed of a material having excellent acoustic characteristics in terms of transmission of ultrasound waves. The end cap 24 is connected to the distal end of a sheathing tube 22a of the above-mentioned flexible cord 22. Provided within the end cap 24 is a rotary cradle 25 which supports thereon an ultrasound transducer element 26. The rotary cradle 25 is connected to a flexible rotation transmission shaft 22b in the form of tightly wound transmission coils which are passed through the sheathing tube 22a of the flexible cord 22. Further, a cable 27 which is connected to the ultrasound transducer element 26 is passed internally of the flexible transmission shaft 22b.

Figure 4:
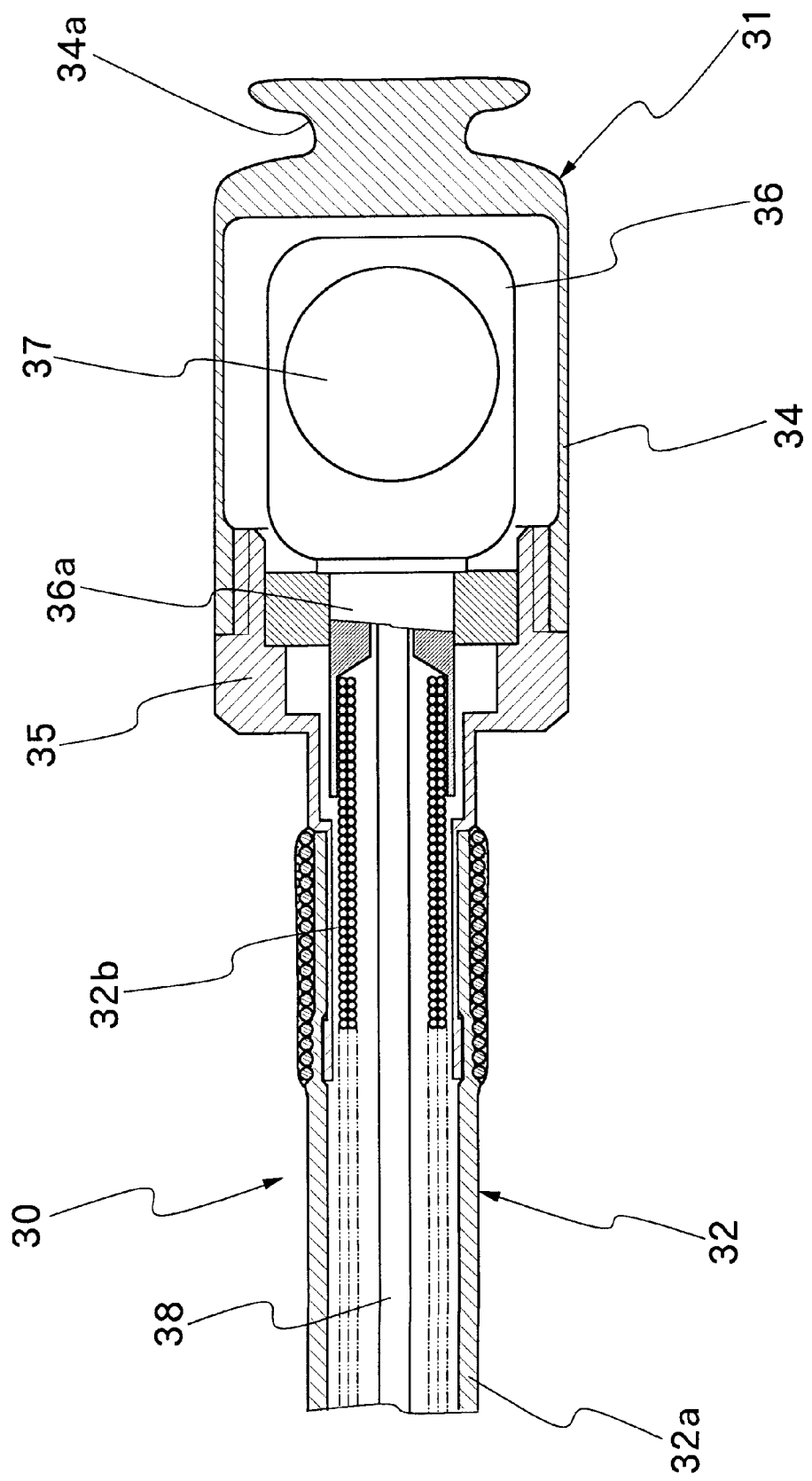
FIG. 4 is a schematic sectional view of a fore end portion of a second type of ultrasound probe.

Shown in FIG. 4 is the construction of the scanner head 31 of the ultrasound probe 30 of the second type. In the case of the bulky ultrasound scanner head 31, an end cap 34 similarly of excellent acoustic characteristics is connected to a fore distal end of a sheathing tube 32a of the flexible cord 32 through a joint ring 35. An ultrasound transducer element 37 is mounted on a rotary cradle 36 which is rotatably provided in the end cap 34. Through a rotational shaft 36a, the rotary cradle 36 is connected to a flexible rotation transmission shaft 32b which is fitted in the sheathing tube 32a of the flexible cord 32. A cable 38 which is connected to the ultrasound transducer element 37 is passed internally of the flexible transmission shaft 32b. An annular balloon anchoring groove 34a is formed around a distal end portion of the end cap 34 having an increased wall thickness.

The tail end connectors 23 and 33 of the above-described ultrasound probes 20 and 30 may be arranged in either same or different constructions.

Figure 5:
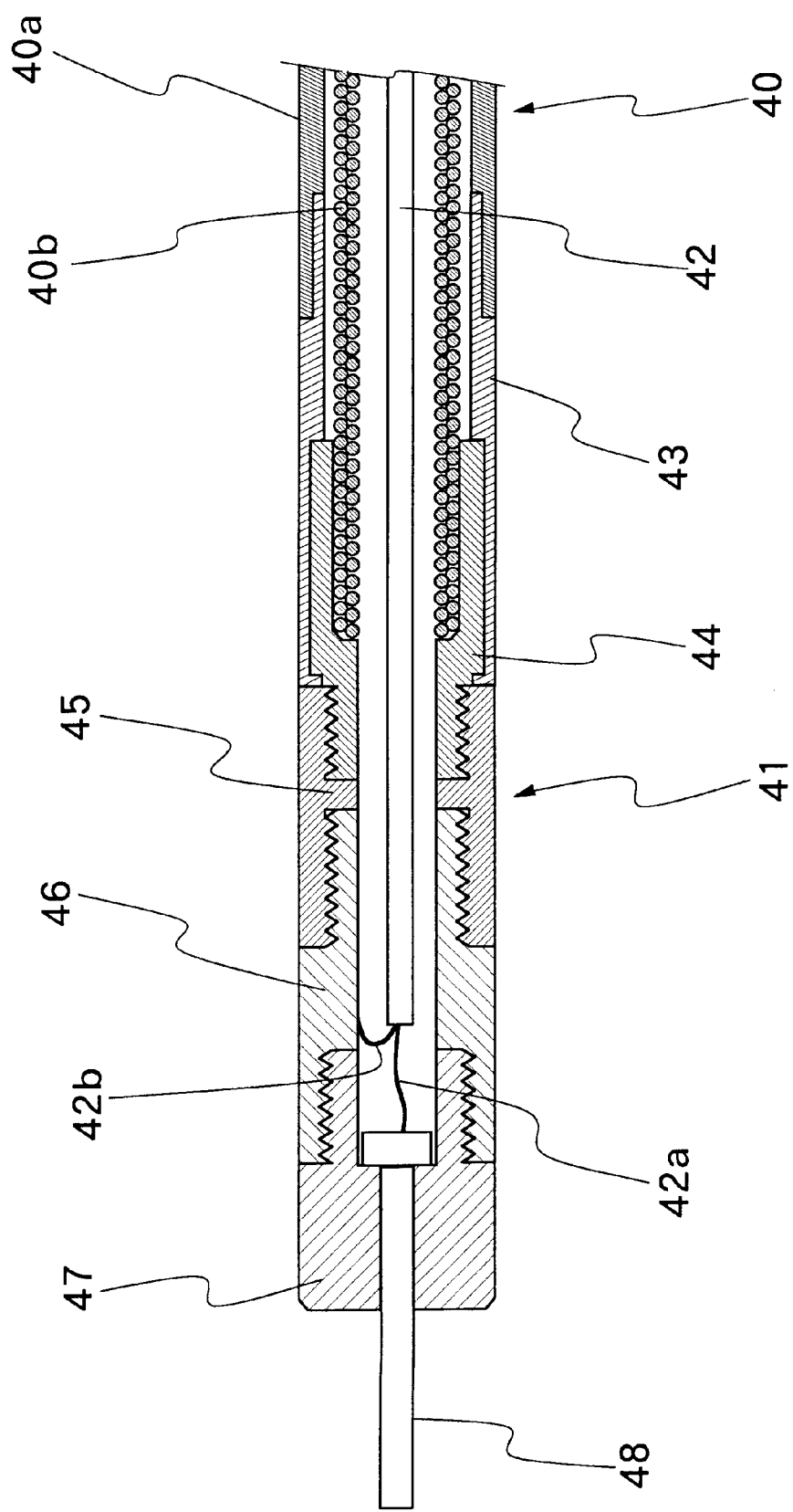
FIG. 5 is a schematic sectional view of a proximal base end portion of an ultrasound probe.

In the particular instances given herein, the tail end connectors 23 and 33 are identical with each other in construction and, for example, are arranged as shown in FIG. 5. In that figure, flexible cord and tail end connector portions which are common to the two different types of ultrasound probes are designated by reference numerals 40 and 41, respectively. The flexible cord 40 is largely constituted by a sheathing tube 40a and a flexible transmission shaft 40b which is fitted in the sheathing tube 40a. A cable 42 is passed axially and internally of the flexible transmission shaft 40b.

The proximal end of the sheathing tube 40a is connected to a rigid pipe 43, while the proximal end of the flexible transmission shaft 40b is securely fixed to a rotational drive ring which constitutes a rotating member of the connector. A first insulating ring 45 and a conductive ring 46 are successively connected to the proximal end of the rotational drive ring 44 by screws or other suitable connection means. Similarly, a second insulating ring 47 is connected to the fore end of the rotational drive ring 44. The cable 42 is extended into the conductive ring 46 through the rotational drive ring 44 and first insulating ring 45, and divided into a core wire 42a and a shield wire 42b within the conductive ring 46. The core wire 42a is connected to an electrode pin 48 which is planted in the second insulating ring 47, while the shield wire 42b is connected to the conductive ring 46. Accordingly, the rotational drive ring 44, first insulating ring 45, conductive ring 46 and second insulating ring 47 are rotationally coupled with a rotational shaft on the scanner drive unit 14a of the relay means 14 by splining or other means which prohibits relative rotational movements. The electrode pin 48 and conductive ring 46 are connected to a pair of electrodes which are provided on the rotational shaft just mentioned.

With the construction as described above, the connector can be detachably connected to the rotational shaft on the scanner drive unit 14a. Therefore, upon rotationally driving that rotational shaft, the ultrasound transducer element is put in rotation at the time of a radial scan. At the same time, the cable from the ultrasound transducer element is electrically connected to an electrical coupling member on the side of the rotational shaft, which in turn is connected to the ultrasound image observation terminal 12 through a rotary connector. These arrangements are known in the art and therefore are omitted in the drawings and in the following description.

Figure 6:
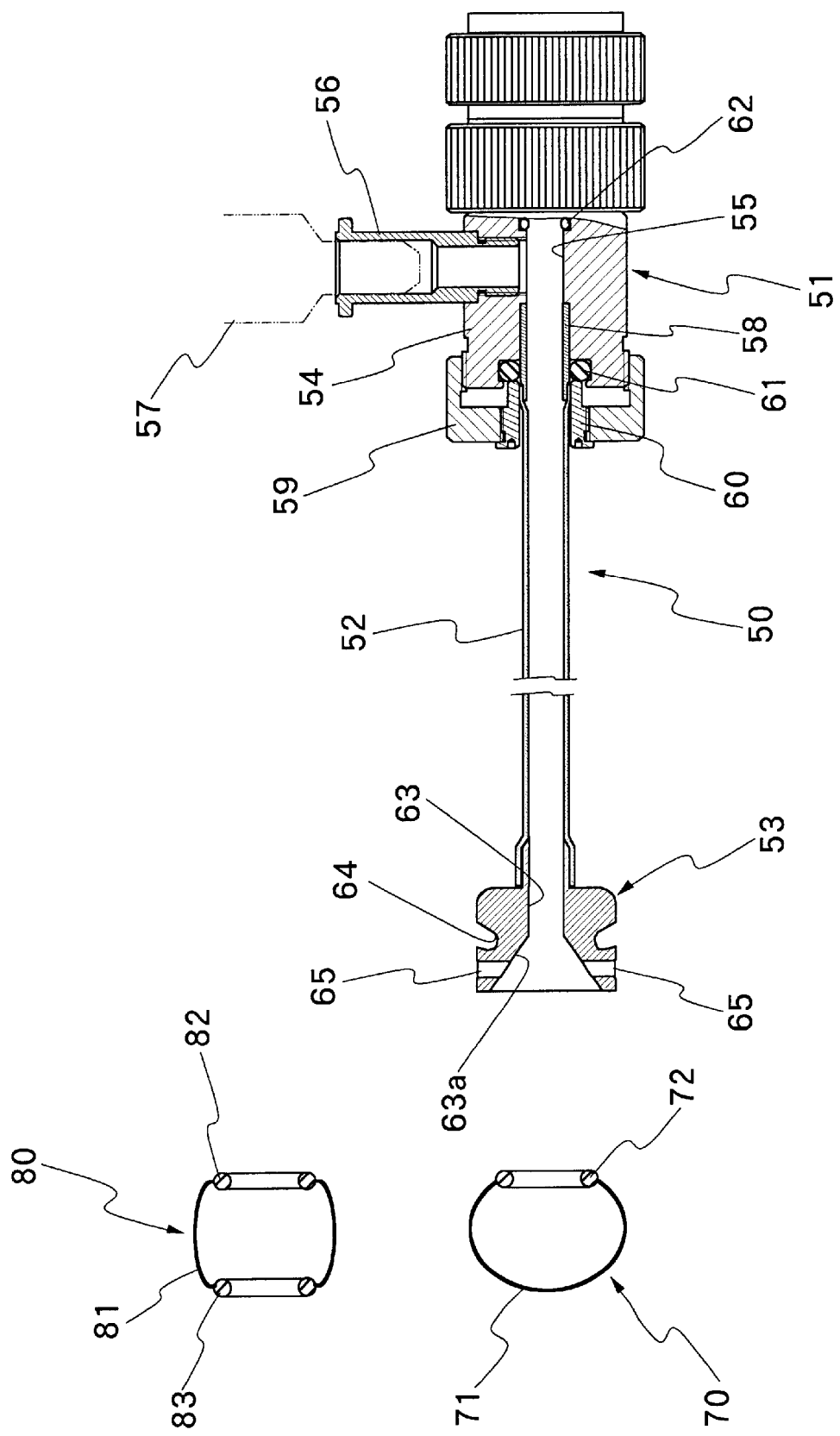
FIG. 6 is a schematic sectional view of the balloon anchor device.

Each one of the ultrasound probes 20 and 30 is placed in the endoscopic biopsy channel 5 not directly but through a balloon anchor device 50 which is set in the endoscopic biopsy channel 5 beforehand. FIGS. 2 and 6 show the balloon anchor device 50 in outer and sectional views, respectively. As seen in these figures, the balloon anchor device 50 includes a liquid feeder mechanism 51, a flexible anchor tube 52 and a balloon support member 53. The liquid feed mechanism 51 serves to supply an ultrasound transmitting medium into a balloon, and provided with an axial passage hole within a casing 54 for passing an ultrasound probe therethrough. A proximal end portion of the casing 54 is detachably attached to the scanner drive unit 14a of the relay means 14 along with the probe. A syringe or other liquid feed means is detachably connectible to a tubular liquid inlet pipe 56 which is projected on a lateral side of the liquid feeder section 51, at the time of sending deaerated water or other ultrasound transmitting medium into a balloon.

The anchor tube 52 is employed to function as an internal passage structure and formed of a synthetic resin tube. Connected to the proximal end of the anchor tube 52 is a connector pipe 58 of a rigid material like metal. The connector pipe 58 is detachably connected to the liquid feeder section 51 by means of a connecting ring 59 which is threaded onto an external screw portion in a fore end portion of the casing 54 of the liquid feeder section 51. Further, a pusher pipe 60 is threaded into the connecting ring 59. Fitted on the inner periphery of the casing 54 is a resilient fixation ring 61 which is formed of a resilient material. The connecting ring 59 is threaded onto the casing 54 after inserting the connector pipe 58 through the pusher pipe 60 and resilient ring 61. In doing so, the resilient ring 61 is deformed into a smaller diameter and as a result held into intimate contact with the connector pipe 58 as it is pushed by the inner end of the pusher pipe 60. By the resilient gripping force of the resilient ring 61, the connector pipe 58 is fixed to the liquid feeder section 51 in a hermetically sealed state. Further, an O-ring 62 is fitted in the probe passage 55 on the proximal side of the liquid inlet pipe 56. When the ultrasound probe 20 or 30 is inserted into the balloon anchor device, the O-ring 62 is abutted against the circumference of the flexible cord 22 or 32 to provide a seal therearound.

The elongated anchor tube 52 has an outside diameter smaller than inside diameter of the endoscopic biopsy channel 5, so that it can be smoothly placed in the endoscopic biopsy channel 5. On the other hand, the inside diameter of the anchor tube 52 is larger than outside diameter of the flexible cord 22 or 32 of the probe. Accordingly, as the flexible cords 22 and 32 placed in the anchor tube 52, an annular passage is formed therebetween to enable supply of ultrasound transmitting medium. The balloon support member 53 which is connected to the fore distal end of the anchor tube 52 has a cylindrical body of a predetermined length. The body of the balloon support member 53 has a larger outside diameter as compared with the endoscopic biopsy channel 5, and is internally provided with an axial passage 63. On the proximal side which is connected to the anchor tube 52, the axial passage 63 of the balloon support member 53 is formed substantially in the same inside diameter as the anchor tube 52. On the front side, the axial passage 63 of the balloon support member 53 is gradually diverged toward its fore distal end by a continuously tapered surface 63a. Further, the balloon support member 53 is provided with an annular balloon stopper groove 64 on and around its outer periphery. On the front side of the balloon stopper groove 64, a plural number of radial ports which are in communication with the axial passage 63 are opened on the outer periphery of the balloon support member 53.

The balloon anchor device 50 of the above-described construction is placed and set in the biopsy channel 5 of the endoscope 1 prior to insertion into a body cavity. At this time, the liquid feeder member 51 is separated from the anchor tube 52 by loosening the clamp ring 61 and the connector ring 59, and the proximal end of the anchor tube 52, with the connector pipe 58, is inserted into the endoscopic biopsy channel 5 from the front side, drawing out the proximal end of the anchor tube 52 through the entrance housing 6 and connecting same with the liquid feeder member 51. Thereafter, a balloon is fitted on the balloon support member 53 in case observation by the ultrasound examination system 10 is required. The balloon is fitted on the ultrasound scanner head of the probe in the manner as shown in FIG. 7 in case the ultrasound examination system 10 employs the ultrasound probe 20 and in the manner as shown in FIG. 8 in case of the ultrasound probe 30.

Figure 7:
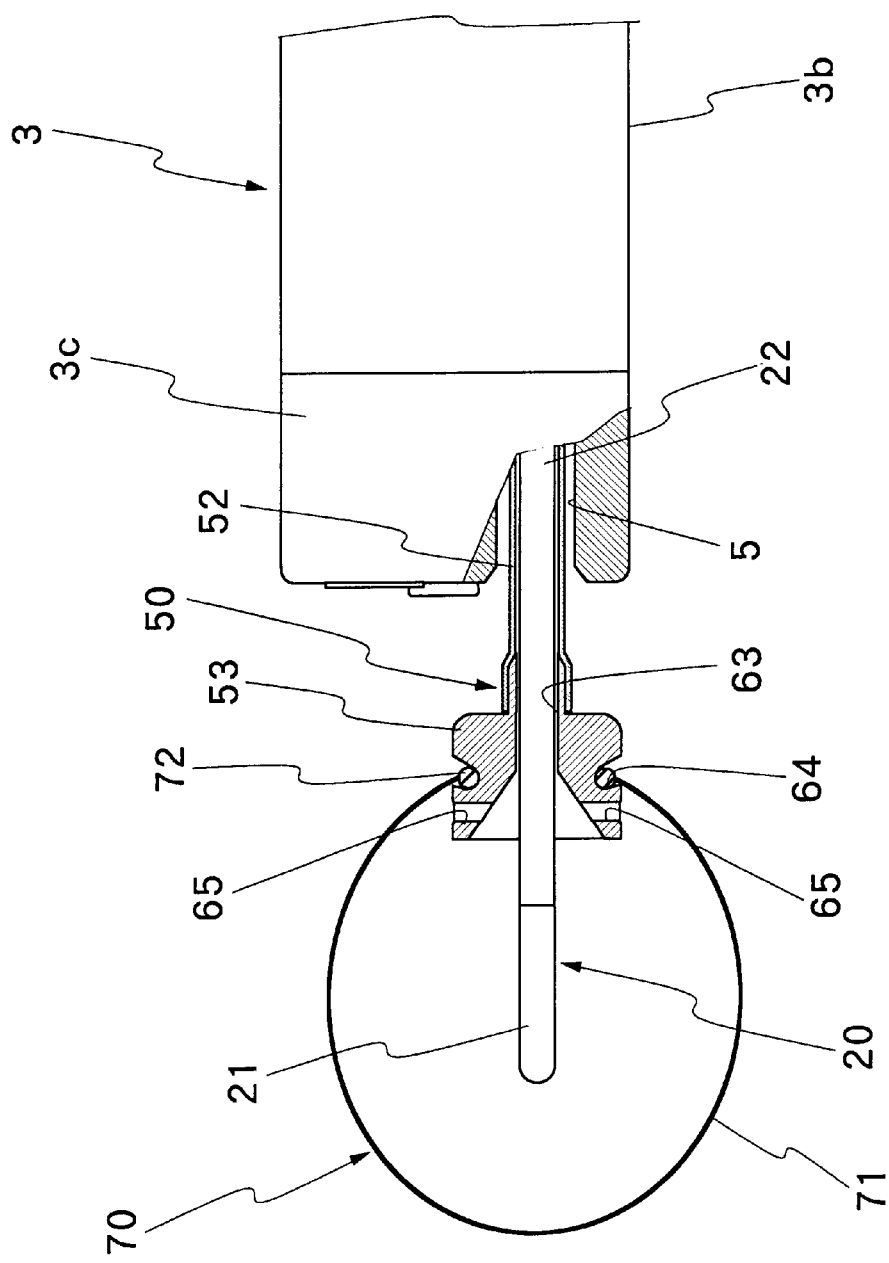
FIG. 7 is a schematic sectional view of the first type of ultrasound probe shown in FIG. 3, which is placed in a biopsy channel of an endoscope along with the balloon anchor device, showing a balloon in an inflated state.
Figure 8:
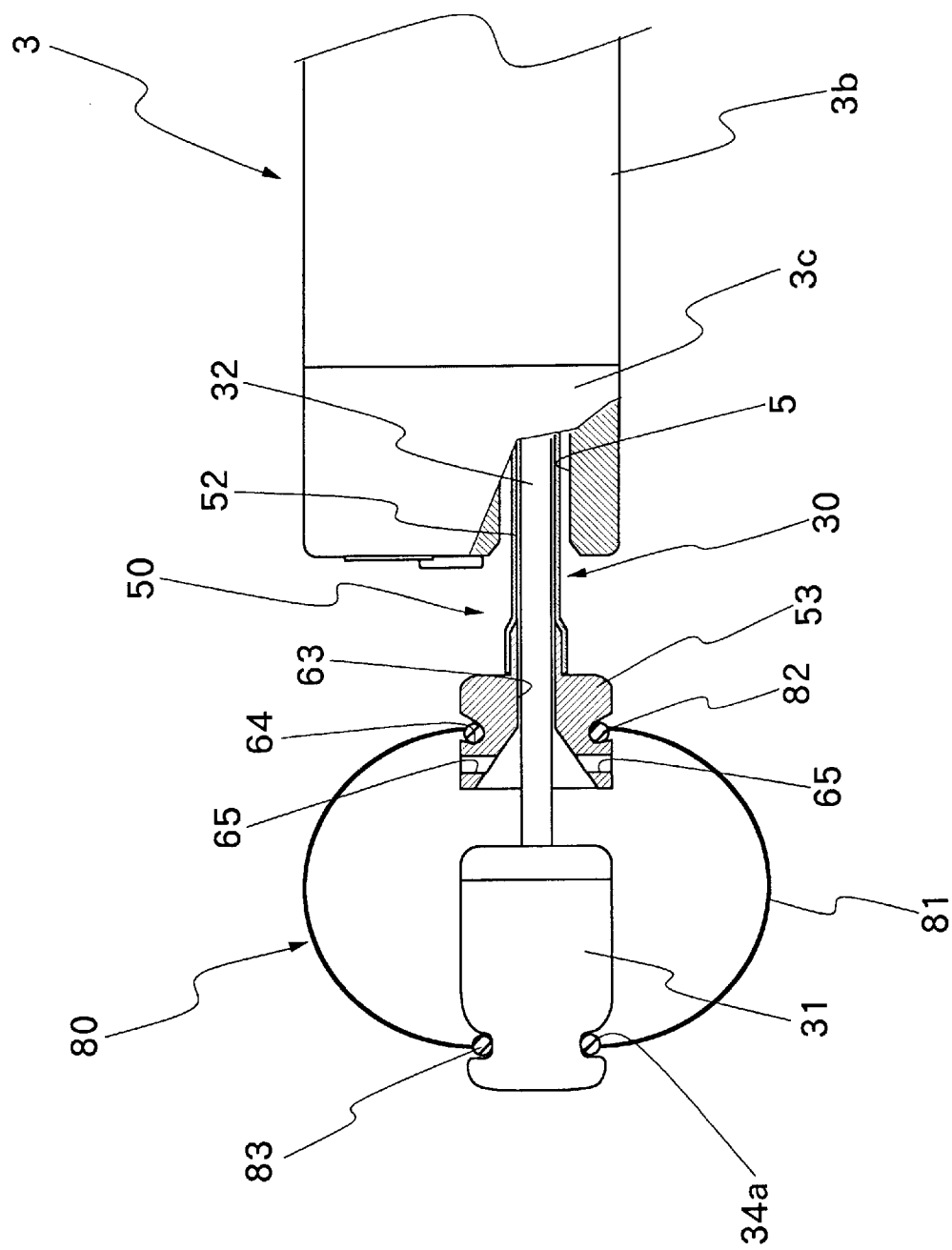
FIG. 8 is a schematic sectional view of the second type of ultrasound probe shown in FIG. 4, which is placed in a biopsy channel of an endoscope along with the balloon anchor device, likewise showing a balloon in an inflated state.

In the case of the ultrasound probe 20 shown in FIG. 7, no balloon stopper is provided on the part of the ultrasound scanner head 21 because the ultrasound scanner head 21 is formed in the same outside diameter as the flexible cord 22 and narrower than the anchor tube of the balloon anchor device 50. Besides, the ultrasound probe 20 can be placed in the endoscope after inserting the latter into a body cavity. In contrast, in the case of the ultrasound probe 30 shown in FIG. 8, since the ultrasound scanner head 31 is larger in diameter than the endoscopic biopsy channel 5, it is necessary for the ultrasound probe 30 to be placed in the balloon anchor device 50 before introducing the insertion instrument 3 of the endoscope into a body cavity. In this case, since the balloon stopper groove 34a is provided on the end cap 34 of the ultrasound scanner head 31, a balloon is fitted around the scanner head in a bridged fashion between the balloon anchor device 50 and a distal end portion of the end cap 34.

As will be understood from the foregoing description, balloon of different forms are used for the ultrasound probes 20 and 30.

As shown also in FIG. 6, a balloon 70 of a bag shape is used in the case of the ultrasound probe 20. More specifically, the balloon 70 consists of a bag which is formed of a flexible membrane of latex or the like, and a resilient stopper ring 72 which is provided around the open end of the bag. The balloon 70 is set on the balloon anchor device 50 by fitting the lip-like resilient ring 70 in the annular groove 64 on the balloon support member 53. The ultrasound probe 20 may be placed in the balloon anchor device 50 before inserting the endoscopic insertion instrument 3 into a body cavity. Alternatively, if necessary, it may be placed into the balloon anchor device 60 after inserting the endoscopic insertion instrument into a body cavity.

On the other hand, in the case of the ultrasound probe 30, the abovedescribed balloon 70 may be used. In this case, however, considering radial scans by the ultrasound transducer element 37, it is desirable to use the balloon 80 as shown in FIG. 6 which can be inflated into a cylindrical shape keeping a uniform distance from the outer periphery of the end cap 34. The balloon 80 consists of a tubular membrane of latex or the like having resilient stopper rings 82 and 83 at and around the opposite open ends thereof. In use, the resilient ring 82 is hermetically fitted in the annular groove 64 on the balloon support member 53, while the other resilient ring 83 is hermitically fitted in the groove 34a on the end cap 34 of the ultrasound scanner head 31. Accordingly, when using the ultrasound probe 30, it is placed and set in the endoscope along with the balloon anchor device before introducing the endoscopic insertion instrument 3 into a body cavity under examination.

The balloon 70 or 80 is retained in a contracted state until the insertion instrument 3 of the endoscope 1 has been inserted into an intracavitary examination site. When it becomes necessary to make an ultrasound scan on a diseased or suspected portion which has been found as a result of an endoscopic examination, the liquid feed means 57 is connected to the liquid inlet 56 to send an ultrasound transmitting medium such as deaerated water, for example, into the anchor tube 52. Whereupon, deaerated water is allowed to flow toward the fore distal end of the balloon anchor device through the gap spaces between the flexible cord 2 or 32 and the anchor tube 53 and the axial passage 63 of the balloon support member 53 and then into the balloon 70 or 80 which is fitted on the balloon support member 53. As a result, the flexible membrane 71 or 81 of the balloon is inflated and brought into intimate contact with an intracavitary wall. In this regard, when using the ultrasound probe 30, the ultrasound scanner head 31 could obstruct the flow passage of deaerated water if it is abutted against the balloon support member 53. In that case, however, deaerated water is allowed to flow into the balloon 80 through the radial communication ports 65 in an assured manner. In this state, the ultrasound transducer element 26 or 37 is activated to scan an intracavitary region of interest. In so doing, since there is no air gap in the path of ultrasound transmission and reception, attenuation of ultrasound signals can be suppressed to a minimum to obtain ultrasound images of high quality in terms of S/N ratio.

In the case of the ultrasound probe 20, it is possible to use a larger size for the flexible membrane 71 because the balloon support member 53 is larger than the ultrasound scanner head 21 of the ultrasound probe 20 in outside diameter as described above. Besides, the annular stopper groove 64 on the balloon support member 53 can be formed to a greater depth. Therefore, even if a large quantity of deaerated water is supplied to the balloon 70, there is little possibility of the resilient ring 72 coming off the annular groove 64 under the weight of supplied deaerated water.

Further, the opposite ends of the balloon anchor device 50 are opened when the anchor tube 52 is separated from the liquid feeder section 51. It follows that the balloon 70 and the anchor tube 52 can be entirely filled with deaerated water completely free of air, for example, by fitting the balloon 70 on the balloon anchor device in a submerged state within a deaerated water tank. On the other hand, in the case of the balloon 80, after placing the ultrasound probe 30 in the balloon anchor device 50, the balloon 80 can be likewise filled with deaerated water completely free of air by fitting same around the ultrasound scanner head similarly in a submerged state. Accordingly, the balloon can be inflated completely free of air upon feeding deaerated water from the liquid feed means 57, making is possible to eliminate the troublesome operation of removing entrained prior to ultrasound scans.

Figure 9:
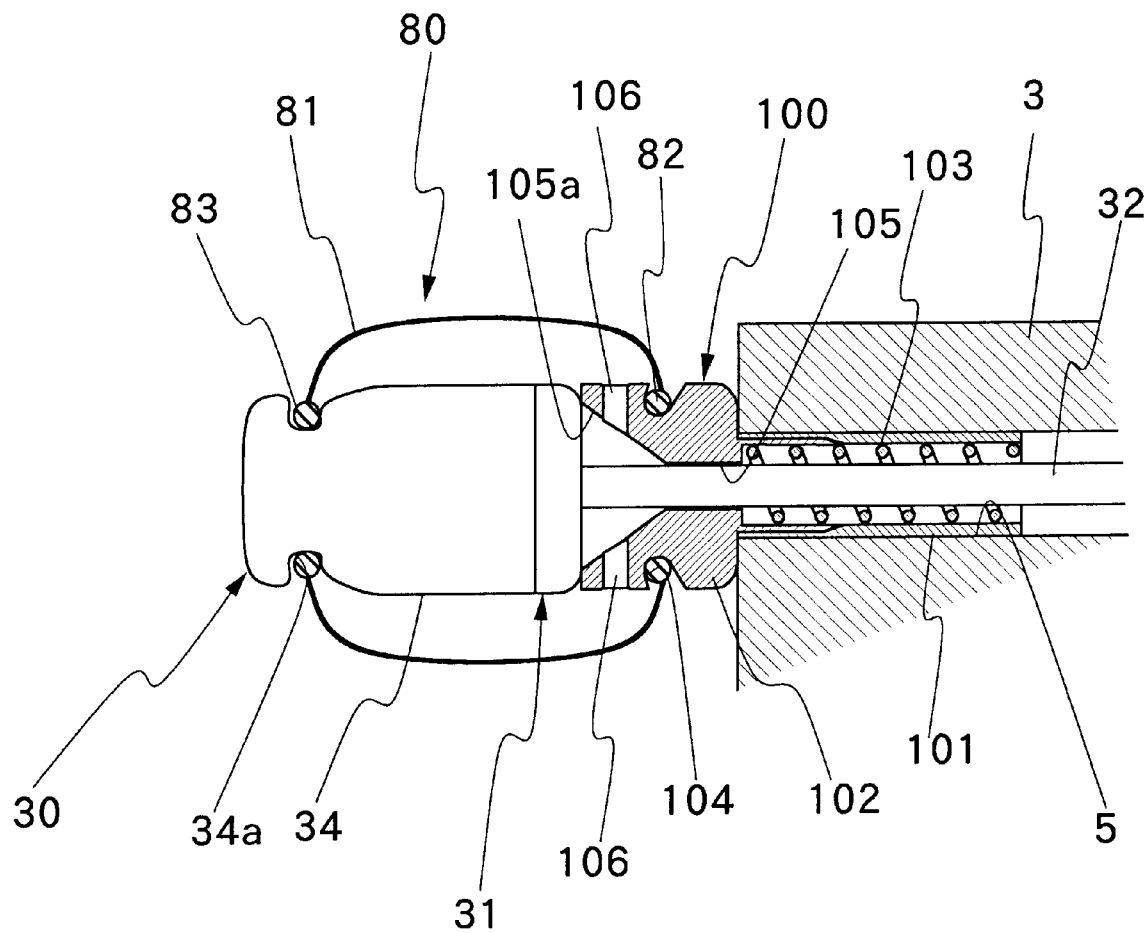
FIG. 9 is a schematic sectional view of the balloon anchor device holding an inflated balloon fixedly in position on and around an ultrasound probe scanning head.
Figure 10:
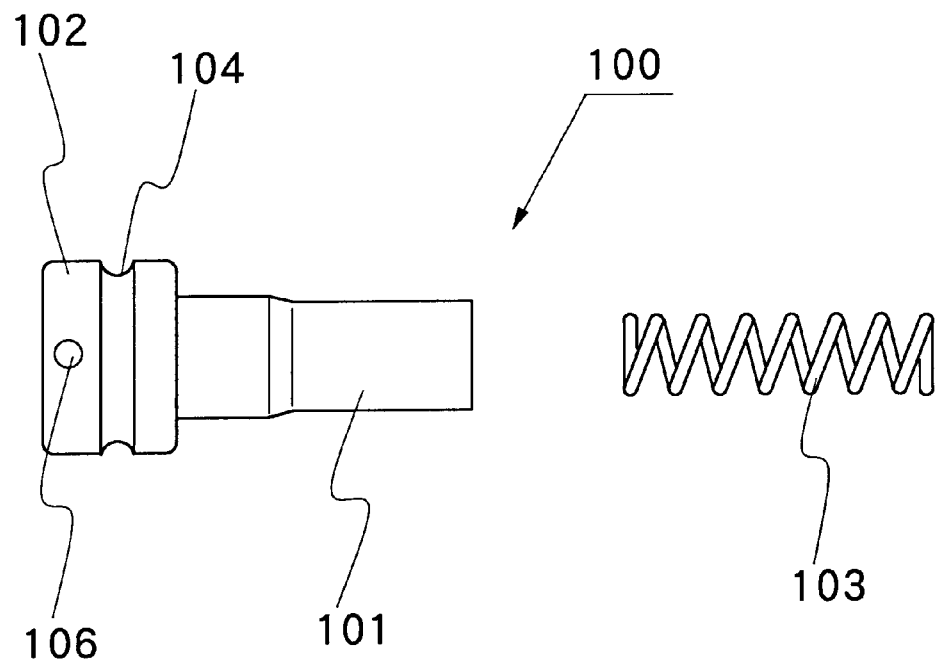
FIG. 10 is an exploded view of the balloon anchor device.

Referring now to FIGS. 9 and 10, there is shown a modification of the balloon anchor device according to the present invention. In these figures, indicated at 100 is a balloon anchor device which similarly includes a flexible anchor tube 101 to be placed in an endoscopic biopsy channel as a liquid passage and a balloon support member 102. In addition, a gap-forming member 103 is fitted in the anchor tube 101. In the particular embodiment shown, the balloon anchor device 100 is described in relation with the second type of ultrasound probe 30 having the ultrasound scanner head 31 which is larger than the inside diameter of the biopsy channel 5 of the endoscope 1. Needless to say, the balloon anchor device 100 can be used for anchoring in position the balloon 70 on the first type of ultrasound probe 20.

The flexible anchor tube 102 is formed of a resilient material like rubber to have an outside diameter larger than the inside diameter of the endoscopic biopsy channel 5.

Therefore, the anchor tube 101 is deformed into a contracted state when placed into the endoscopic biopsy channel 5 through the entrance housing on the manipulating head grip of the endoscope. On the other hand, the inside diameter of the anchor tube 101 is larger than the outside diameter of the flexible cord 32 of the ultrasound probe 30. The balloon support member 102 has an annular body of a predetermined thickness, having an outside diameter substantially same as or slightly smaller than that of the ultrasound scanner head 31 of the probe 30. Formed around the outer periphery of the balloon support member 102 is an annular stopper groove 104 for fitting engagement with the resilient stopper ring 82 of the balloon 80. Contiguously on the front side of the flexible anchor tube 101, a probe receptacle passage 105 is formed axially and centrally through the balloon support member 102. Fore end portion of the probe receptacle passage 105 is forwardly spread to provide a tapered or beveled surface 105a. One or plural number of radial communication ports, each in communication with the probe receptacle passage 105, are opened on the outer periphery of the balloon support member 102 on the front side of the annular stopper groove 104. If desired, the balloon support member 102 may be provided as an integral part of the flexible anchor tube 101. However, considering the function of anchoring the balloon 80 fixedly in position, the balloon support member 102 is preferred to be formed of a rigid material and fixedly connected to the flexible anchor tube 101 of a resilient material.

The inside diameters of the flexible anchor tube 101 and the probe receptacle passage 105 of the balloon support member 102, which receive the flexible cord 32 of the ultrasound probe 30, are determined such that gap spaces of suitable width are formed around the flexible cord 32 as a passage for the ultrasound transmitting medium. Accordingly, the gap-forming member 103 functions as a biasing means which presses the flexible anchor tube 101 against the inner periphery of the endoscopic biopsy channel 5, securing an open fluid passage between the flexible cord 32 and the flexible anchor tube 101. For this purpose, the gap-forming member 103 is constituted by a coil which, in a natural or free state, has an outside diameter slightly larger than the flexible anchor tube 101 placed in the endoscopic biopsy channel 5. Even when fitted in the flexible anchor tube 101, the coil of the gap-forming member 103 has an inside diameter which is large enough for receiving the flexible cord of the probe. Besides, the coil of the gap-forming member is coarsely pitched to provide fluid passages between the helices of the coil.

Figure 11:
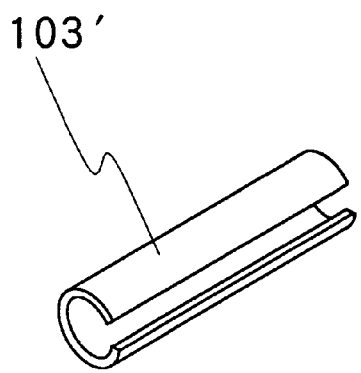
FIG. 11 is a schematic outer view of a gap-forming member of a modified construction.

Alternatively, there may be employed a gap-forming member 103' in the form of a thin-walled slit pipe of metal and substantially of C-shape in cross section as shown in FIG. 11. In free state, this gap-forming member 103' has an outside diameter slight larger than the inside diameter of the flexible anchor tube 101, and contracted into a smaller diameter at the time of insertion into the flexible anchor tube 101 so that, once fitted in position, it acts to press the anchor tube 101 fixedly against the inner periphery of the endoscopic biopsy channel 5. When the flexible cord 32 of the ultrasound probe is placed in the anchor tube 101, a gap space is formed between the flexible cord 32 and the gap-forming member 103' to provide a passage for deaerated water.

Figure 12:
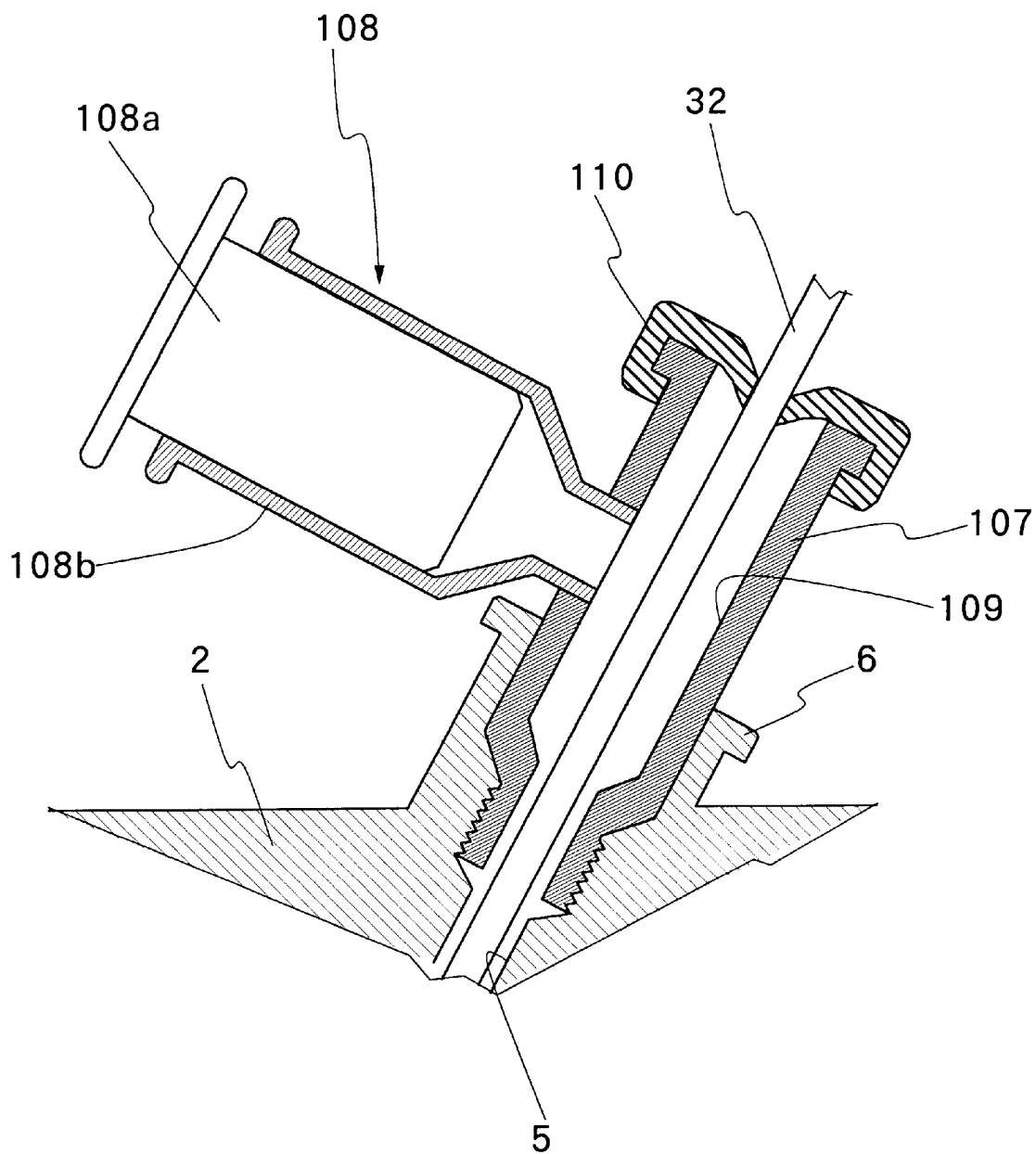
FIG. 12 is a schematic sectional view of a deaerated water feed means.

Shown in FIG. 12 is an exemplary construction of a deaerated water feeder means which is connected to the balloon anchor device 100 to supply thereto deaerated water as an ultrasound transmitting medium. As seen in that figure, in this instance, the medium feeder means includes a connector pipe 107, and a deaerated water pumping member which is projected on a lateral side of the connector pipe 107 and constituted by a piston 108a and a cylinder 108b. The connector pipe 107 is internally provided with an axial receptacle passage 109 to receive the flexible cord 32 therein. A seal member 110 is fitted on the proximal end of the connector pipe 107, which is located on the outer side of the deaerated water feed member 108. The seal member 110 is provided with an aperture in its concavely curved center portion which can hold the circumference of the inserted flexible cord substantially in a sealed state. As the pressure on the side of the internal passage 109 is increased, the seal member 110 is more tightly pressed against the flexible cord 32 to provide a tighter seal therearound. The connector pipe 107 is fixable to the entrance housing 6 by screws or other suitable fixation means. Accordingly, upon pushing in the piston 108a of the deaerated water feed member 108, deaerated water in the cylinder 108b is pumped into the endoscopic biopsy channel 5. this instance, before introducing the insertion instrument 3 of the endoscope 1 into a body cavity, the ultrasound probe 30 is placed and set in the endoscope 1 along with the balloon anchor device 100. A balloon is fitted on and between the balloon anchor device 100 and the ultrasound probe 11 preferably under deaerated water in a tank. Generally, a valve is provided within a length of a suction passage which is connected to the endoscopic biopsy channel 5, so that vacuum pressure prevails in the suction passage upon opening that valve, causing deaerated water to quickly flow into the endoscopic biopsy channel 5 to replace air completely. In this state, the gap-forming member 103 is fitted into the flexible anchor tube 101 and pushed into the opening at the fore distal end of the endoscopic biopsy channel. This can be done outside the deaerated water tank. Similarly, after separation from the relay means, the connector portion 32 of the ultrasound probe 30 is immersed in deaerated water in the tank, along with the connector pipe 107 to introduce deaerated water into the cylinder 108 of the pumping member 108.

Thereafter, from the connector at the tail end, the ultrasound probe 30 is inserted into the probe passage 105 in the balloon support member 102 of the balloon anchor device 100 which is fitted in the fore distal end of the endoscopic biopsy channel 5. After being passed through the entire length of the endoscopic biopsy channel 5, the tail end connector is drawn out through the entrance housing 6 on the endoscope until the ultrasound scanner head 31 is abutted against the fore end face of the balloon support member 102. In this state, the tail connector portion of the ultrasound probe 30 is passed through the connector pipe 107 and the seal member 110, and the connector pipe 107 is fixed in position by threading same into the entrance housing 6. As a consequence, the ultrasound probe 30 is placed in position within the endoscope.

Then, a balloon 80 is fitted on the ultrasound scanner head 32 of the probe 30. More particularly, the balloon 80 is fitted on also under deaerated water in a tank. Of the resilient stopper rings 82 and 83 which are provided at the front and rear ends of the balloon 80, the resilient ring 82 is anchored in the annular stopper groove 104 on the outer periphery of the balloon support member 102 and the other resilient ring 83 is anchored in the annular stopper groove 34a on the end cap 34 of the ultrasound scanner head 31. By fitting the balloon 80 on, the balloon anchor device is hermetically closed and filled with deaerated water completely free of air in its entire length from the balloon 80 to the connector pipe 107. Besides, as the flexible cord 32 of the ultrasound probe 30 is pulled outward of the endoscopic biopsy channel 5 to a certain extent, the balloon support member 102 of the balloon anchor device 100 is gripped between the ultrasound scanner head 32 and the fore open end of the endoscopic biopsy channel 5 and stably retained at the fore end of the endoscope.

The balloon 80 is retained in a contracted state as long as no pressure is externally applied on the piston 108a of the deaerated water feed member 108. The balloon is in the contracted state when the insertion instrument 3 of the endoscope 1 is introduced into a body cavity and while an intracavitary region of interest is being examined through the endoscopic observation system. In case a diseased portion is found by an endoscopic examination, it is further examined by an ultrasound scan or scans. In preparation therefor, firstly the piston 108a of the deaerated water feed member 108 is pushed into the cylinder 108b. Whereupon, deaerated water in the cylinder 108 is pushed forward to flow toward the endoscopic biopsy channel 5, more particularly, to flow in the toward direction into the anchor tube 101 since the proximal end of the connector pipe 107 is closed with the seal member 110. Through the flow passage which is formed by the gap-forming member 103 (or 103') between the flexible anchor tube 101 and the flexible cord 32 of the probe, deaerated water is admitted into the balloon anchor device 100 and allowed to flow out through the radial communication ports 106 into the balloon 80 which is fitted around the end cap 34. As a result, the balloon 80 is inflated and brought into intimate contact with an opposing intracavitary wall.

In the various embodiments described above, preferably a balloon is fitted on the balloon anchor device in a submerged state within a deaerated water tank for the purpose of precluding air or air bubbles which would otherwise get into the anchor device. However, if desired, the balloon anchor device may include an air escape mechanism for expelling air out of a balloon which is fitted on the balloon anchor device. Shown in FIGS. 13 and 14 are balloon anchor devices with such air escape mechanism.

Figure 13:
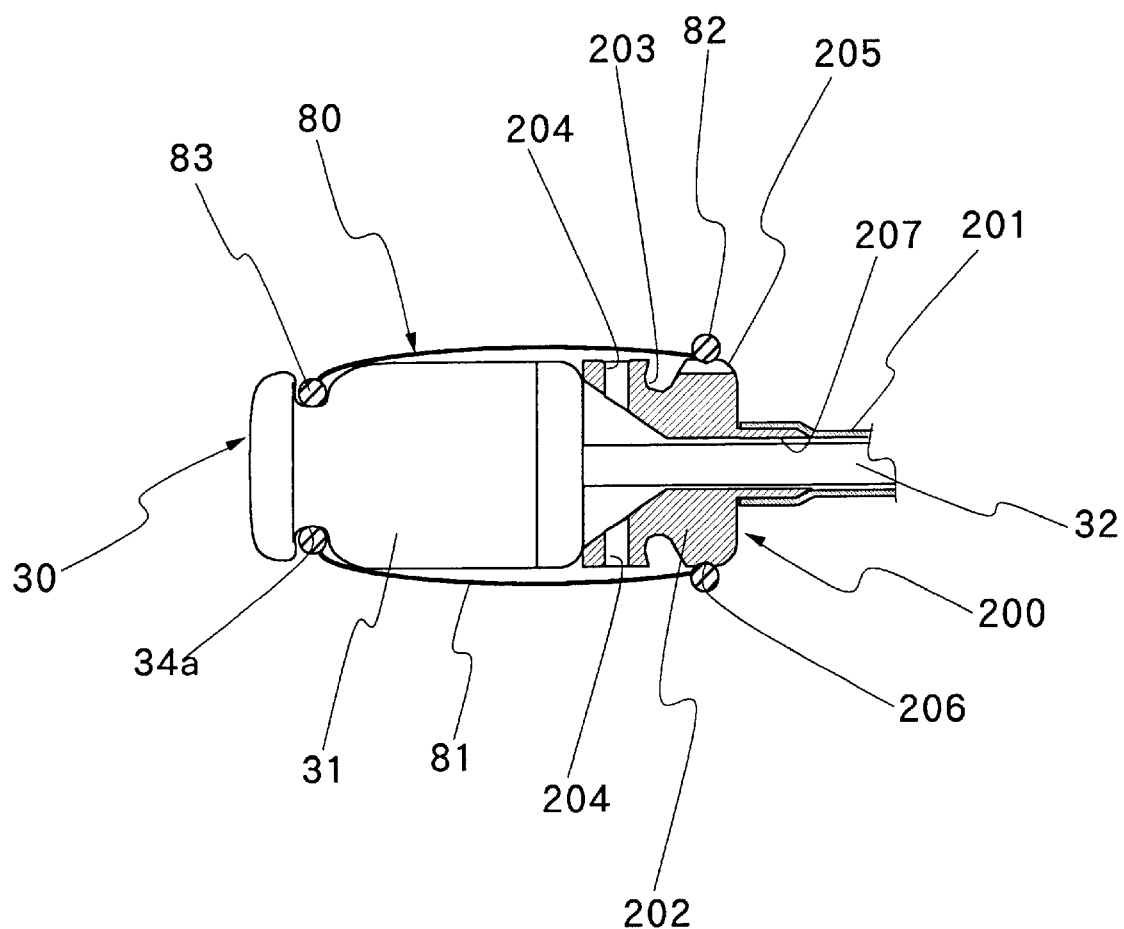
FIG. 13 is a schematic illustration of an ultrasound probe which is placed in a biopsy channel of an endoscope along with a balloon anchor device which is provided with an air escape mechanism for expelling air from a balloon, the air escape mechanism being shown in a position for expelling air out of the balloon.

More specifically, shown in FIG. 13 is a balloon anchor device 200 of a construction similar to the first embodiment described hereinbefore. In this instance, a balloon support member 202, which is connected to the fore distal end of a flexible cord 201 of the ultrasound probe, is provided with a straight air escape groove 205 axially and contiguously on the proximal side of an annular balloon stopper groove 203, that is to say, on the side away from radial communication ports 204. The straight air escape groove 205 is shallower than the annular stopper groove 203 in depth. The balloon support member 202 is further provided with an annular resilient ring holder portion 206 across the straight air escape groove 205. This resilient ring holder portion 206 is in the form of an annular groove which is far shallower than the annular balloon stopper groove 203 and the straight air escape groove 205. At the time of putting a balloon on the ultrasound scanner head 31, one resilient ring 83 is fitted in the stopper groove 34a while the other resilient ring 82 is fitted not in the annular stopper groove 203 but in the ring holder portion 206 on the proximal side. When put on in this way, the inner space of the balloon 80 is communicated with the atmosphere through the straight groove 205. It follows that, when deaerated water is supplied to the balloon 80 through the axial receptacle passage 207 in the balloon support member 202, air in the balloon 80 is allowed to escape to the outside through the straight groove 205. As soon as air is completely expelled, the resilient ring 82 is relocated to the annular stopper groove 203 from the ring holder portion 206. Thus, the balloon 80 is anchored in position in an air-free state.

Figure 14:
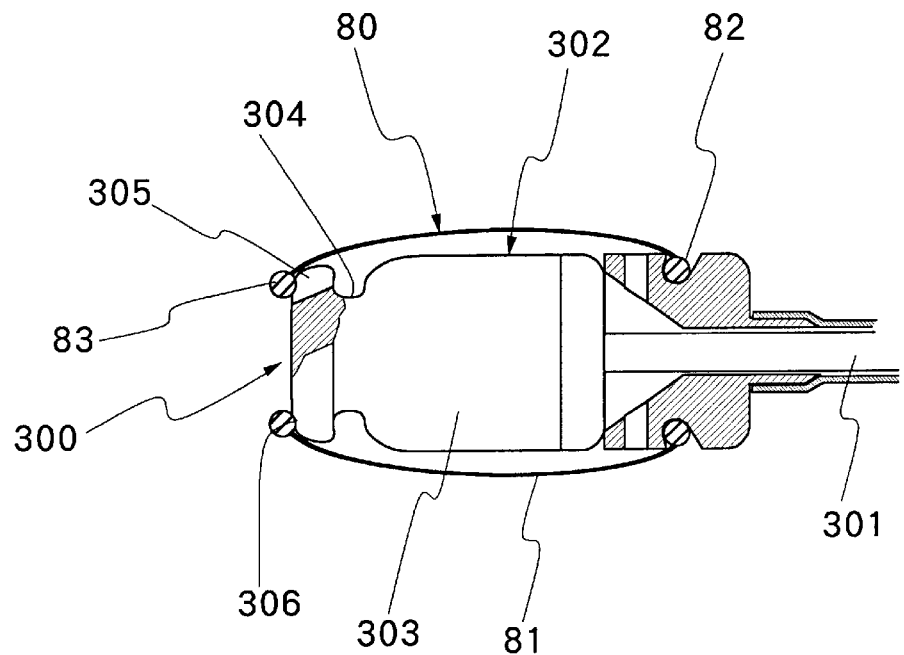
FIG. 14 is a view similar to FIG. 13 but shows another example of the air escape mechanism which is provided on the side of the ultrasound probe.

A straight groove of the nature as described above can be formed on the side where the resilient ring 83 is stopped, as shown in FIG. 14. More specifically, as seen in that figure, a straight air escape groove 305 is provided contiguously on the front side of an annular balloon stopper groove 304 which is formed in a fore end portion of an end cap 303 of an ultrasound scanner head 302 which is in turn connected to the distal end of a flexible cord 301 of an ultrasound probe 300. Likewise, the straight groove 305 is shallower than the annular stopper groove 304. A resilient ring holder portion 306 which is shallower than the straight groove 305 is provided on the distal end face of the end cap 303. The resilient ring holder portion 306 is formed in such a position that at least part of the outer open end of the straight groove 305 is exposed on the distal end face of the end cap 303. Accordingly, the depth of the straight groove 305 is gradually increased toward the distal end of the end cap. These arrangements make it possible to expel air from the balloon 80 substantially in the same manner as in the embodiment shown in FIG. 13.

Alternatively, an air escape mechanism may be provided on the part of a balloon. Namely, for this purpose, there may be employed a balloon which is arranged as shown in FIG. 15 in combination with an ultrasound probe having an end cap as shown in FIG. 16 for its ultrasound scanner head.

Figure 15:
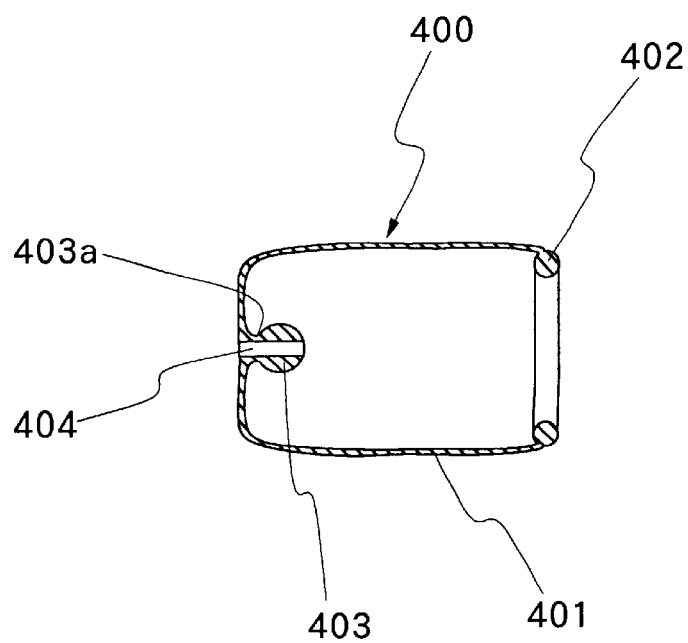
FIG. 15 is a schematic sectional view of a balloon which is provided with an air escape mechanism.

More particularly, as seen in FIG. 15, in addition to a resilient stopper ring 402 which is provided at and around an open base end of a bag-like flexible membrane 401, a balloon 400 is provided with a spherical inward projection 403 on the inner side of its closed fore end. The spherical inner projection 403 is formed of the same resilient material as and connected to the flexible membrane 401 through a constricted neck portion 403a, and provided with a through hole 404 of a circular shape in cross section substantially at its center portion. In addition to functions as an air escape mechanism, this spherical inner projection 403 serves as a stopper on the front side of the balloon 400.

Figure 16:
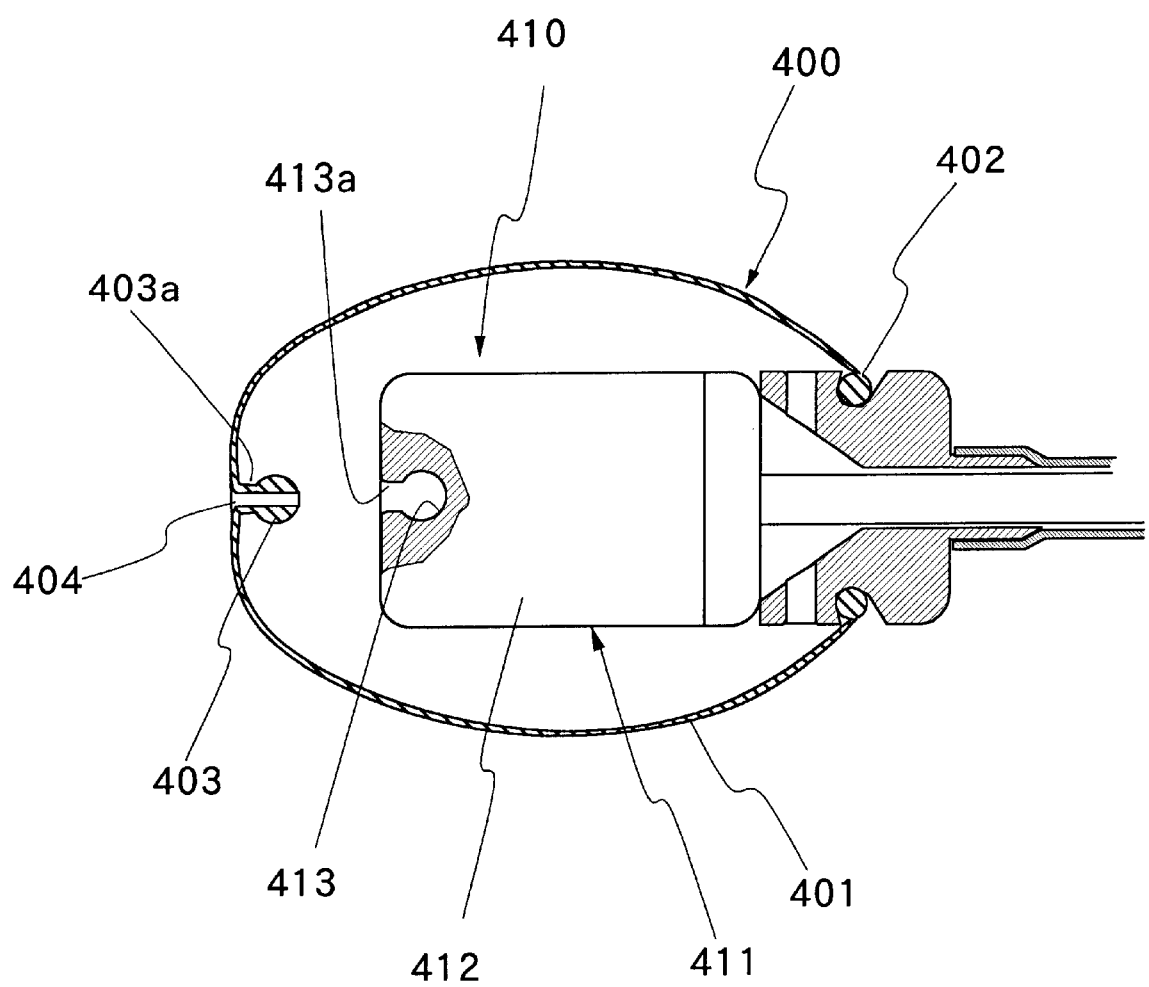
FIG. 16 is a schematic illustration of the balloon of FIG. 15 which is in an air expelling position.

Shown in FIG. 16 is an ultrasound scanner head 411 of an ultrasound probe 410, the ultrasound scanner head 411 having an end cap 412 which is adapted for use with the balloon 400. Namely, the end cap 412 of the ultrasound scanner head 411 is provided with a recess 413 on its fore distal end. The recess 413 is shaped complementarily to the profile of the spherical inner projection 403 but slightly smaller than the latter in size. Complementarily to the neck portion 413a on the part of the spherical projection 404, the recess 413 is provided with a constricted portion 413a at its outer open end. Consequently, when the spherical projection 403 is resiliently fitted into the recess 413 on the end cap 412, its spherical outer surface is tightly engaged with the inner surface of the recess 413. Besides, by the constricted portion 413a of the recess 413, the spherical projection 403 is retained in the recess 413 in a stably fixed state even when the internal pressure of the balloon 400 is increased by introduction thereto of deaerated water.

With the arrangements just described, although not shown in the drawings, firstly the resilient ring 40 is fitted in the annular groove on the balloon support member of the balloon anchor device, and then deaerated water is supplied to the balloon 400 with the spherical inner projection 403 still separated from the end cap 412 of the ultrasound scanner head 411, allowing air to escape to the outside through the center hole 404 of the spherical projection 403. After completely expelling water out of the balloon 400, the spherical inner projection 403 is snapped in the recess 413 of the end cap 412 to fix the fore end of the balloon 400 to the latter.

Figure 17:
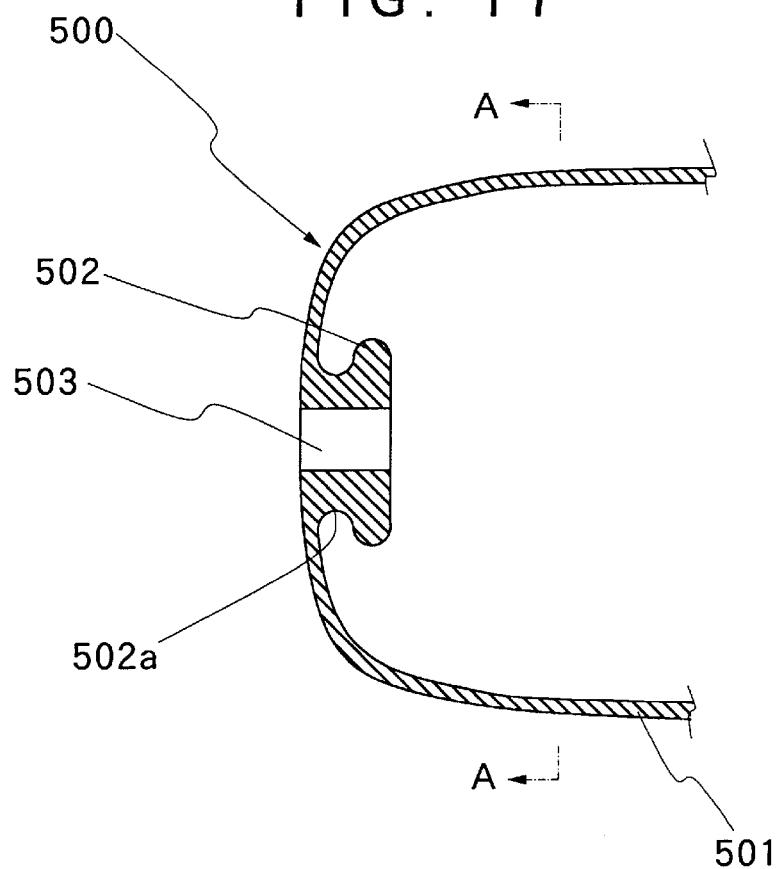
FIG. 17 is a fragmentary sectional view of another example of a balloon with an air escape mechanism.
Figure 18:
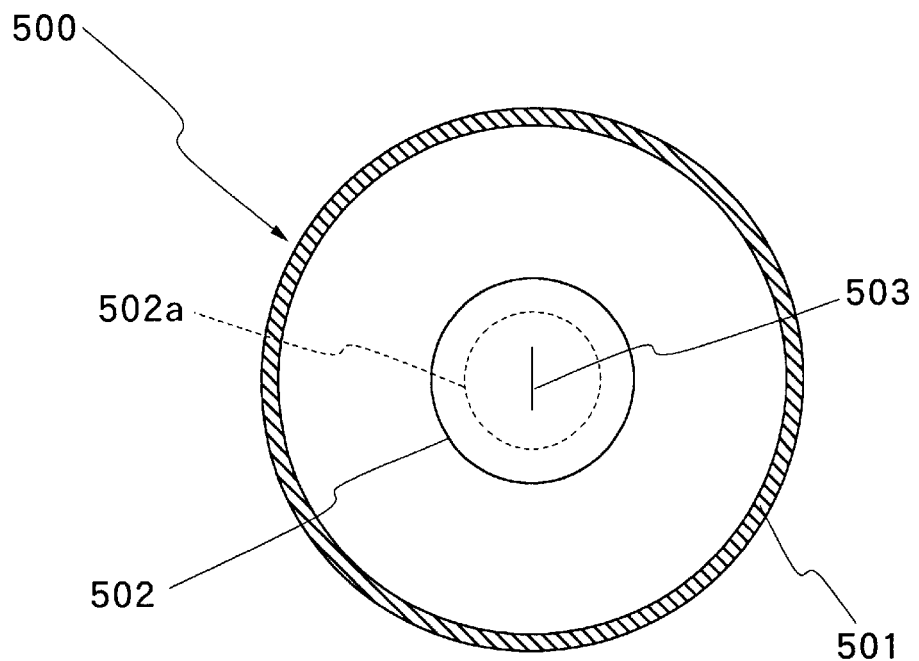
FIG. 18 is a schematic sectional view taken on line A—A of FIG. 17.

Alternatively, in place of the balloon 400 with the spherical inner projection as described above, there may be employed a balloon 500 which is provided with a tubular projection 503 on the inner side of the fore closed end of its bag-like membrane 501 as shown in FIGS. 17 and 18. The tubular projection is provided with a constricted small diameter portion 502a on the outer side of a thick flanged portion 502 which is formed at and around its inner end. A radial slit 503 is cut into the tubular inner projection throughout the entire axial length of the latter. When the inner flanged end 502 of the tubular inner projection is subjected to a force or pressure acting in compressing direction, the slit 503 is spread open, forming an air escape passage for expelling air in the balloon 500 to the outside therethrough. As soon as the external compressive force or pressure is removed, the slit 503 is closed in a hermetically sealed state. In this instance, although not shown in the drawings, a recess of a profile complementary to the flanged inner end 502 is provided on the fore distal end of the end cap of the ultrasound scanner head to stop the inner projection therein in a similar manner.

What is claimed is:

1. A balloon anchor for use with an endoscopically inserting ultrasound probe for stopping a balloon having at least one resilient ring fixedly and hermetically on and around an ultrasound scanner head provided at a fore distal end of a flexible cord of said ultrasound probe and accommodating an ultrasound transducer element for insertion into a body cavity through a biopsy channel of an insertion instrument of an endoscope, said balloon anchor comprising:

an anchor tube member internally defining an anchor tube passage of an anchor tube passage diameter larger than said flexible cord of said ultrasound probe and configured to be placed in said endoscopic biopsy channel along with said flexible cord therein, said anchor tube member having a fore end portion projected through an opening at a fore distal end of said endoscopic biopsy channel; and a balloon support member connected to the projected fore end portion of said anchor tube member and having;

a rigid cylindrical body of a body diameter larger than said endoscopic biopsy channel, a balloon support passage of a balloon support passage diameter larger than said flexible cord, said balloon support passage being contiguous with a front end of said anchor tube passage, and an annular balloon anchor groove provided on an outer periphery of said balloon support member to fixedly anchor therein said resilient ring of said balloon;

wherein a fluid passage being formed around said flexible cord by said anchor tube passage and said balloon support passage, said fluid passage allowing supply of an ultrasound transmitting medium to said balloon fixedly anchored in said annular balloon anchor groove of said balloon support member.

2. A balloon anchor as defined in claim 1, wherein said balloon support member further comprises at least one radial communication port in communication with said balloon support passage, said at least one radial communication port being opened on the outer periphery of said balloon support member in at least one position on the front side of said annular balloon anchor groove.

3. A balloon anchor as defined in claim 2, wherein said balloon support passage in said balloon support member is tapered in a forwardly diverging shape in a fore end portion thereof, and said radial communication ports are bored into tapered inner surfaces of said balloon support passage.

4. A balloon anchor as defined in claim 1, wherein said anchor tube member comprises:

a flexible tube passed through said endoscopic biopsy channel having a liquid feed section connected to a proximal end portion which is led out from said endoscopic biopsy channel.

5. A balloon anchor as defined in claim 4, wherein said liquid feed section comprises a liquid feed mechanism housed in a casing and detachably connected to said anchor tube member, said liquid feed mechanism being detachably connectable to an external liquid feeder.

6. A balloon anchor as defined in claim 1, wherein said ultrasound probe has a substantially uniform outside diameter from said flexible cord to said ultrasound scanner head, while said anchor tube passage as well as said balloon support passage in said balloon support member have said anchor tube passage diameter and said balloon support passage diameter larger than said outside diameter of said ultrasound probe, and a balloon to be stopped in said annular balloon anchor groove on said balloon support member is in the form of a bag-like elastic membrane having said resilient ring at and around an open end thereof for engagement in said annular balloon anchor groove.

7. A balloon anchor as defined in claim 1, wherein:

said ultrasound probe is equipped with an ultrasound scanner head of a larger diameter than an inside diameter of said endoscopic biopsy channel, while said anchor tube passage as well as said balloon support passage in said balloon support member have said anchor tube passage diameter and said balloon support passage diameter larger than said flexible cord of said ultrasound probe but smaller than said ultrasound scanner head; and said balloon to be stopped in said annular balloon anchor groove on said balloon support member includes a tubular membrane having resilient rings at opposite open ends, one of said resilient rings being anchored in said annular balloon anchor groove on said balloon support member and another one of said resilient rings being anchored in an annular stopper groove formed on said ultrasound scanner head.

8. A balloon anchor as defined in claim 1, wherein said anchor tube member is configured to be fitted in said endoscopic biopsy channel over a predetermined length from a fore distal end of the latter.

9. A balloon anchor as defined in claim 8, further comprising a gap-forming member fitted in said anchor tube member to secure a flow passage of said ultrasound transmitting medium between an inner periphery of said anchor tube passage and said flexible cord of said ultrasound probe received in said anchor tube passage.

10. A balloon anchor as defined in claim 9, wherein said gap-forming member comprises a resilient metallic structure capable of producing a biasing force to press said flexible cord against an inner periphery of said anchor tube channel.

11. A balloon anchor as defined in claim 9, wherein said gap-forming member comprises a metal coil with helices wound in a predetermined pitch.

12. A balloon anchor as defined in claim 10, wherein said gap-forming member comprises a thin-walled metal pipe substantially of C-shape in cross section having an inside diameter larger than said flexible cord of said ultrasound probe.

13. A balloon anchor as defined in claim 4, wherein said liquid feed section is detachably connected to an entrance housing of said endoscopic biopsy channel.

14. A balloon anchor as defined in claim 1, wherein said anchor tube member is placed in said endoscopic biopsy channel such that said balloon support member is projected forward from said endoscopic biopsy channel along with said ultrasound probe fitted into said fluid passage, said balloon support member being provided with an air escape mechanism for expelling air out of said balloon anchored on and around an outer periphery thereof.

15. A balloon anchor as defined in claim 14, wherein said air escape mechanism comprises an axial straight groove provided on said outer periphery of said balloon support member and extended to a proximal end thereof across said annular balloon anchor groove.

16. A balloon anchor as defined in claim 14, wherein said air escape mechanism comprises an axial straight groove provided in a fore end portion of said ultrasound scanner head of said probe and extended toward a fore distal end thereof across a second annular balloon anchor groove.

17. A balloon anchor as defined in claim 14, wherein:
- said balloon is an elastic membrane of bag-like shape closed at one end; and
- said air escape mechanism comprises an inner projection formed on an inner side of said closed end of said membrane, said inner projection containing an air passage in communication with the atmosphere and being fixedly fitted in a recess provided on said ultrasound scanner head of said probe after expelling air out of said balloon.

\* \* \* \* \*